United States Patent
Locke et al.

(10) Patent No.: US 8,172,818 B2
(45) Date of Patent: May 8, 2012

(54) REDUCED-PRESSURE, LIQUID-COLLECTION CANISTER WITH MULTI-ORIENTATION FILTER

(75) Inventors: Christopher Brian Locke, Bournemouth (GB); Aidan Marcus Tout, Ringwood (GB); Benjamin Andrew Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 280 days.

(21) Appl. No.: 12/478,244

(22) Filed: Jun. 4, 2009

(65) Prior Publication Data

US 2009/0306630 A1    Dec. 10, 2009

Related U.S. Application Data

(60) Provisional application No. 61/058,830, filed on Jun. 4, 2008.

(51) Int. Cl.
*A61M 1/00* (2006.01)
(52) U.S. Cl. ......... 604/319; 604/313; 604/317; 604/540
(58) Field of Classification Search ................. 604/317, 604/319; 600/364; 210/90, 94, 645, 646
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |

(Continued)

FOREIGN PATENT DOCUMENTS
AU         550575 A1    8/1982

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986); pp. 94-96.

(Continued)

*Primary Examiner* — Melanie Hand
(74) *Attorney, Agent, or Firm* — SNR Denton US, LLP

(57) ABSTRACT

A reduced pressure treatment system includes a liquid-collection canister for collecting liquid from a tissue site to which reduced pressure treatment is applied. The canister includes a first space configured to collect the liquid from the tissue site and a filter having a frame and a non-planar filter element. The filter defines a second space within the canister separated from the first space by the filter element. The filter element substantially prevents liquid from passing from the first space into the second space. The filter element substantially allows gaseous communication between the first space and the second space when the second space is exposed to a reduced pressure.

19 Claims, 10 Drawing Sheets

U.S. PATENT DOCUMENTS

| | | |
|---|---|---|
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,093,230 A | 7/2000 | Johnson, III et al. |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0099343 A1* | 7/2002 | Garcia ............................ 604/313 |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0178360 A1 | 9/2003 | Haldopoulos et al. |
| 2004/0122434 A1* | 6/2004 | Argenta et al. .................. 606/86 |
| 2004/0225208 A1* | 11/2004 | Johnson ........................ 600/364 |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1 234 589 A | 8/2002 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2007/133618 A2 | 11/2007 |
| WO | WO 2008/100438 A | 8/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul 1987, vol. 165 pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989 pp. 59-63.

Egnell Minor, Instruction Book, First Edition 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukio, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986) pp. 369-370.

D.E. Tribble, An Improved Sump Drain-Irrigation Device of Simple Construction, *Archives of Surgery of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax,"*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

International Search Report and Written Opinion date mailed Oct. 14, 2009 for PCT International Application No. PCT/US2009/046244.

\* cited by examiner

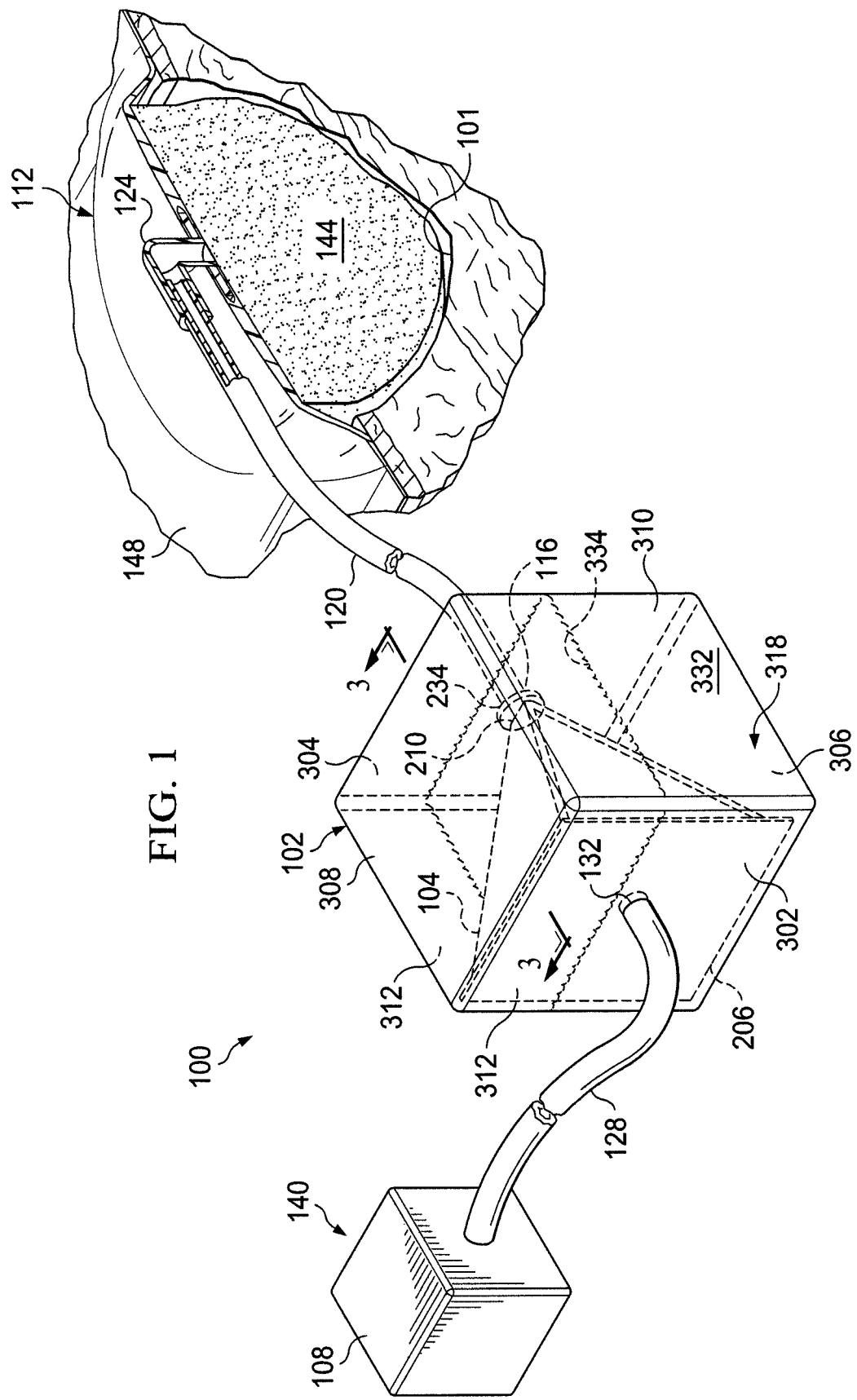

REDUCED-PRESSURE, LIQUID-COLLECTION CANISTER WITH MULTI-ORIENTATION FILTER

CROSS-REFERENCE TO RELATED APPLICATIONS

This application claims the benefit of U.S. Provisional Application No. 61/058,830, filed Jun. 4, 2008, which is hereby incorporated by reference.

BACKGROUND OF THE INVENTION

1. Field of the Invention

The present invention relates generally to reduced pressure treatment systems and more particularly to a reduced-pressure, liquid-collection canister having a filter that allows operation of the canister in multiple orientations.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

SUMMARY

The problems presented by existing reduced pressure systems and liquid-collection canisters are solved by the systems and methods of the illustrative embodiments described herein. A liquid-collection canister for collecting liquid from a tissue site to which reduced pressure treatment is applied includes a first space configured to collect the liquid from the tissue site. A filter having a frame and a non-planar filter element is provided. The filter defines a second space within the canister separated from the first space by the filter element. The filter element substantially prevents liquid from passing from the first space into the second space. The filter element substantially allows gaseous communication between the first space and the second space when the second space is exposed to a reduced pressure.

In another illustrative embodiment, a liquid-collection canister for collecting liquid from a tissue site to which reduced pressure treatment is applied includes a first space and a second space. The first space is configured to collect the liquid from the tissue site, and the second space is configured to receive a reduced pressure. A plurality of liquid-air separators are positioned within the canister between the first space and the second space such that the liquid in the first space is substantially prevented from entering the second space. The plurality of liquid-air separators allows transfer of a gas between the second space and the first space. At least two of the plurality of liquid-air separators are substantially planar and each of the two are located within different planes.

In still another illustrative embodiment, a liquid-collection canister for collecting liquid from a tissue site to which reduced pressure treatment is applied includes a first space configured to collect the liquid from the tissue site. The canister further includes a filter disposed on a wall of the canister. The filter has a first chamber extending from the wall of the canister and includes an opening at an end of the first chamber opposite the wall. The filter has a second chamber extending from the wall of the canister and includes an opening at an end of the second chamber opposite the wall. The opening of the first chamber allows communication between the first space and the first chamber. The opening of the second chamber allows communication between the first space and the second chamber. A distance from the opening of the first chamber to the wall is greater than a distance from the opening of the second chamber to the wall. A first filter element is positioned over the opening of the first chamber, and a second filter element is positioned over the opening of the second chamber.

In yet another illustrative embodiment, a reduced pressure treatment system for applying reduced pressure treatment to a tissue site includes a liquid-collection canister. The canister comprises a first space configured to collect a liquid from the tissue site and a filter having a frame and a non-planar filter element. The filter defines a second space within the canister separated from the first space by the filter element. The filter element substantially prevents liquid from passing from the first space into the second space. The filter element substantially allows gaseous communication between the first space and the second space. The canister further includes a canister inlet associated with the first space and a canister outlet associated with the second space. A reduced pressure source is provided in fluid communication with the canister outlet to deliver a reduced pressure to the second space. A manifold is positioned at the tissue site and in fluid communication with the canister inlet to distribute the reduced pressure to the tissue site.

In yet another illustrative embodiment, a reduced pressure treatment system for applying reduced pressure treatment to a tissue site includes a liquid-collection canister. The canister includes a first space configured to collect the liquid from the tissue site and a second space configured to receive a reduced pressure. A plurality of liquid-air separators is positioned within the canister between the first space and the second space such that the liquid in the first space is substantially prevented from entering the second space. The plurality of liquid-air separators allows transfer of a gas between the second space and the first space. At least two of the plurality of liquid-air separators are substantially planar, and each of the two are located within different planes. A canister inlet is associated with the first space, and a canister outlet is associated with the second space. A reduced pressure source is in fluid communication with the canister outlet to deliver a reduced pressure to the second space, and a manifold is positioned at the tissue site and in fluid communication with the canister inlet to distribute the reduced pressure to the tissue site.

In another illustrative embodiment, a reduced pressure treatment system for applying reduced pressure treatment to a tissue site includes a liquid-collection canister. The canister includes a first space configured to collect the liquid from the tissue site and a filter disposed on a wall of the canister. The filter has a first chamber extending from the wall of the canister and includes an opening at an end of the first chamber opposite the wall. The filter has a second chamber extending from the wall of the canister and includes an opening at an end of the second chamber opposite the wall. The opening of the first chamber allows communication between the first space and the first chamber. The opening of the second chamber allows communication between the first space and the second chamber. A distance from the opening of the first chamber to the wall is greater than a distance from the opening of the second chamber to the wall. A first filter element is positioned over the opening of the first chamber, and a second filter element is positioned over the opening of the second chamber. A canister inlet allows communication with the first space, and a canister outlet allows communication with the first and second chambers. A reduced pressure source is in fluid communication with the canister outlet to deliver a reduced pressure to the first and second chambers, and a manifold is positioned at the tissue site and in fluid communication with the canister inlet to distribute the reduced pressure to the tissue site.

In still another illustrative embodiment, a method of collecting liquid from a tissue site includes applying a reduced pressure to a second space of a canister. The second space has an opening to allow communication with a first space of the canister. The opening is covered by a non-planar filter element that allows gaseous communication through the non-planar filter element such that the reduced pressure is communicated to the first space of the canister. Liquid is drawn into the first space, and flow through the non-planar filter element is filtered to substantially prevent the liquid from entering the second space.

In yet another illustrative embodiment, a method of collecting liquid from a tissue site includes applying a reduced pressure to a second space of a canister. The second space has a plurality of openings to allow communication with a first space of the canister. The openings are covered by a plurality of liquid-air separators, and at least two of the plurality of liquid-air separators are substantially planar and located within different planes. Gaseous communication is allowed through the liquid-air separators such that the reduced pressure is communicated to the first space of the canister. The liquid is drawn into the first space, and flow through the liquid-air separators is filtered to substantially prevent the liquid from entering the second space.

In another illustrative embodiment, a method of collecting liquid from a tissue site includes applying a reduced pressure to a first chamber and a second chamber of a canister. The first and second chambers each extend from a wall of the canister and each include an opening at an end of the chamber opposite the wall. The opening of the first chamber is covered by a first filter element, and the opening of the second chamber is covered by a second filter element. A distance from the opening of the first chamber to the wall is greater than a distance from the opening of the second chamber to the wall. The method further includes allowing gaseous communication through the first and second filter elements such that the reduced pressure is communicated to a first space of the canister. The liquid is drawn into the first space, and flow through the first and second filter elements is filtered to substantially prevent the liquid from entering the first and second chambers.

In yet another illustrative embodiment, a method of administering reduced pressure treatment to a tissue site includes applying a reduced pressure to a second space of a canister. The second space has an opening to allow communication with a first space of the canister, and the opening is covered by a non-planar filter element. Gaseous communication is allowed through the non-planar filter element such that the reduced pressure is communicated to the first space of the canister. The reduced pressure is communicated to the tissue site. A liquid is drawn from the tissue site into the first space, and flow through the non-planar filter element is filtered to substantially prevent the liquid from entering the second space.

In yet another illustrative embodiment, a method of administering reduced pressure treatment to a tissue site includes applying a reduced pressure to a second space of a canister. The second space has a plurality of openings to allow communication with a first space of the canister. The openings are covered by a plurality of liquid-air separators, and at least two of the plurality of liquid-air separators are substantially planar and located within different planes. The method further includes allowing gaseous communication through the liquid-air separators such that the reduced pressure is communicated to the first space of the canister. The reduced pressure is communicated to the tissue site. A liquid is drawn from the tissue site into the first space, and flow through the liquid-air separators is filtered to substantially prevent the liquid from entering the second space.

In yet another illustrative embodiment, a method of administering reduced pressure treatment to a tissue site includes applying a reduced pressure to a first chamber and a second chamber of a canister. The first and second chambers each extend from a wall of the canister, and each include an opening at an end of the chamber opposite the wall. The opening of the first chamber is covered by a first filter element, and the opening of the second chamber is covered by a second filter element. A distance from the opening of the first chamber to the wall is greater than a distance from the opening of the second chamber to the wall. Gaseous communication is allowed through the first and second filter elements such that the reduced pressure is communicated to a first space of the canister. The reduced pressure is communicated to the tissue site. A liquid is drawn from the tissue site into the first space, and flow through the first and second filter elements is filtered to substantially prevent the liquid from entering the first and second chambers.

Other objects, features, and advantages of the illustrative embodiments will become apparent with reference to the drawings and detailed description that follow.

BRIEF DESCRIPTION OF THE DRAWINGS

FIG. 1 illustrates a perspective view of a reduced pressure treatment system having a liquid-collection canister and a multi-orientation filter according to an illustrative embodiment;

DETAILED DESCRIPTION OF ILLUSTRATIVE EMBODIMENTS

Figure 2A:
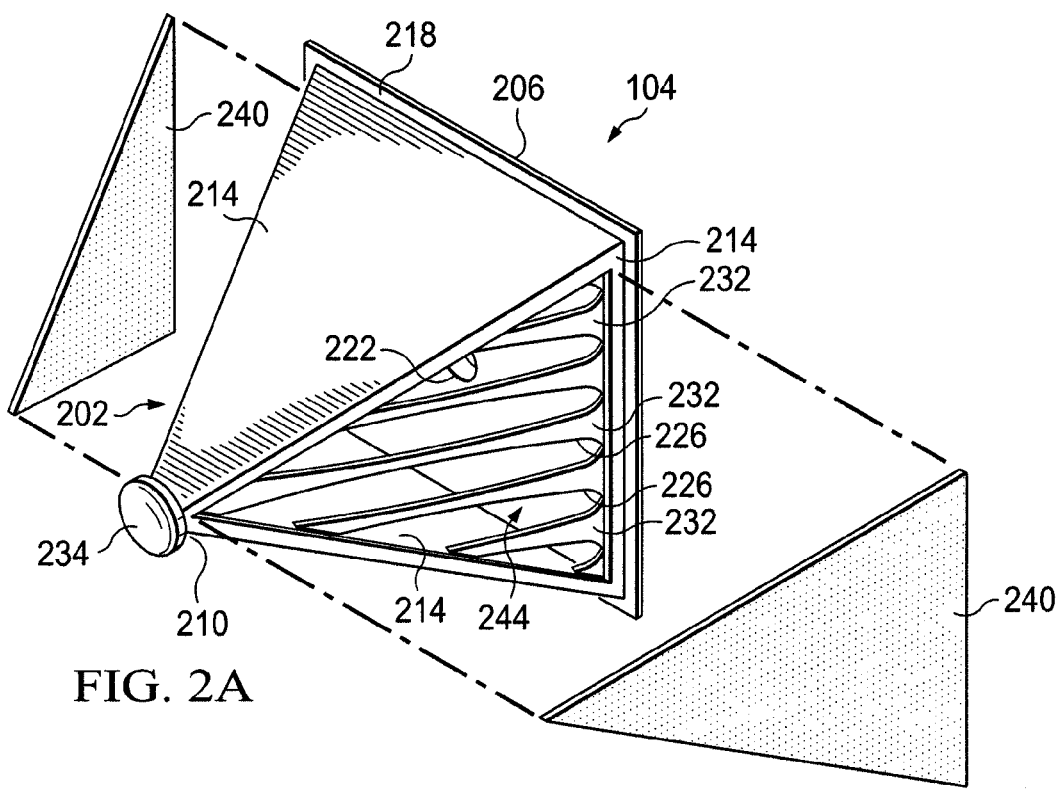
FIG. 2A illustrates an exploded perspective view of the multi-orientation filter of FIG. 1, the filter being pyramid shaped.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Referring to FIG. 1, a reduced pressure treatment system 100 for applying a reduced pressure to a tissue site 101 of a patient according to an illustrative embodiment includes a canister 102 having a filter 104 contained within the canister 102. The canister 102 is positioned in fluid communication with a reduced pressure source 108 and a reduced pressure dressing 112 that is positioned at the tissue site 101. The reduced pressure dressing 112 is fluidly connected to an inlet 116 of the canister 102 by a conduit 120. The conduit 120 may fluidly communicate with the reduced pressure dressing 112 through a tubing adapter 124. A second conduit 128 fluidly connects an outlet 132 of the canister 102 with the reduced pressure source 108.

In the embodiment illustrated in FIG. 1, the reduced pressure source 108 is an electrically-driven vacuum pump. In another implementation, the reduced pressure source 108 may instead be a manually-actuated or manually-charged pump that does not require electrical power. The reduced pressure source 108 instead may be any other type of reduced pressure pump, or alternatively a wall suction port such as those available in hospitals and other medical facilities. The reduced pressure source 108 may be housed within or used in conjunction with a reduced pressure treatment unit 140, which may also contain sensors, processing units, alarm indicators, memory, databases, software, display units, and user interfaces that further facilitate the application of reduced pressure treatment to the tissue site 101. In one example, a sensor or switch (not shown) may be disposed at or near the reduced pressure source 108 to determine a source pressure generated by the reduced pressure source 108. The sensor may communicate with a processing unit that monitors and controls the reduced pressure that is delivered by the reduced pressure source 108.

The reduced pressure dressing 112 includes a distribution manifold 144 adapted to be positioned at the tissue site 101, and a cover 148, or drape, that is positioned over the distribution manifold 144 to maintain reduced pressure beneath the cover 148 at the tissue site 101. The cover 148 may extend beyond a perimeter of the tissue site 101 and may include an adhesive or bonding agent on the cover 148 to secure the cover to tissue adjacent the tissue site 101. In one embodiment, the adhesive disposed on cover 148 may be used to seal between the tissue and the cover 148 to prevent leakage of reduced pressure from the tissue site 101. In another embodiment, a seal layer (not shown) such as, for example, a hydrogel or other material may be disposed between the cover 148 and the tissue to augment or substitute for the sealing properties of the adhesive.

The distribution manifold 144 of the reduced pressure dressing 112 is adapted to contact the tissue site 101. The distribution manifold 144 may be partially or fully in contact with the tissue site 101 being treated by the reduced pressure dressing 112. When the tissue site 101 is a wound, the distribution manifold 144 may partially or fully fill the wound.

The distribution manifold 144 may be any size, shape, or thickness depending on a variety of factors, such as the type of treatment being implemented or the nature and size of the tissue site 101. For example, the size and shape of the distribution manifold 144 may be customized by a user to cover a particular portion of the tissue site 101, or to fill or partially fill the tissue site 101. The distribution manifold 144 may have, for example, a square shape, or may be shaped as a circle, oval, polygon, an irregular shape, or any other shape.

In one illustrative embodiment, the distribution manifold 144 is a foam material that distributes reduced pressure to the tissue site 101 when the distribution manifold 144 is in contact with or near the tissue site 101. The foam material may be either hydrophobic or hydrophilic. In one non-limiting example, the distribution manifold 144 is an open-cell, reticulated polyurethane foam such as GranuFoam® dressing available from Kinetic Concepts, Inc. of San Antonio, Tex.

In the example in which the distribution manifold 144 is made from a hydrophilic material, the distribution manifold 144 also functions to wick fluid away from the tissue site 101, while continuing to provide reduced pressure to the tissue site 101 as a manifold. The wicking properties of the distribution manifold 144 draw fluid away from the tissue site 101 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 144 may further promote granulation at the tissue site 101 when a reduced pressure is applied through the reduced pressure dressing 112. For example, any or all of the surfaces of the distribution manifold 144 may have an uneven, coarse, or jagged profile that causes microstrains and stresses at the tissue site 101 when reduced pressure is applied through the distribution manifold 144. These microstrains and stresses have been shown to increase new tissue growth.

In one embodiment, the distribution manifold 144 may be constructed from bioresorbable materials that do not have to be removed from a patient's body following use of the reduced pressure dressing 112. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 144 may further serve as a scaffold for new cell-growth, or a scaffold material may be used in conjunction with the distribution manifold 144 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Referring still to FIG. 1, but also to FIG. 2A, the filter 104 includes a frame 202 that is pyramid-shaped and includes a base 206, an apex 210, and four walls 214 extending between the base 206 and the apex 210. The base 206 may include a flange 218 to allow the filter 104 to be easily mounted within the canister 102 to a wall of the canister 102. A passage 222 may be positioned in the base 206 to provide fluid communication with the outlet 132 of the canister 102. The frame 202 includes openings 226 in at least two of the four walls 214. In the embodiment illustrated in FIG. 2A, the openings 226 are disposed in only two of the four walls 214, and the openings 226 are positioned in opposing walls. In another embodiment, the openings 226 may be disposed in two adjacent walls 214, or alternatively in three or even four of the four walls 214. It should also be noted that, while the frame 202 illustrated in FIG. 2A is pyramid-shaped with four walls, the frame 202 may be provided in a similar tapered configuration (i.e. tapering from a base to an apex) and instead include only three walls. In another embodiment, the frame 202 may include five walls or an even greater number of walls, with openings 226 in two or more of the walls.

As illustrated in FIG. 2A, multiple openings 226 may be disposed in each wall 214 that includes openings, thereby forming ribs 232 between the openings 226. The openings 226 may be of any shape or size including, without limitation, circular, square, rectangular, ovular, polygonal, irregular, or any other shape.

The filter 104 further includes filter elements 240 to cover the openings 226 in the walls 214 that include openings 226. In the embodiment illustrated in FIG. 2A, the filter element 240 covering each wall 214 is substantially planar, although in alternative embodiments, non-planar filter elements may by used depending on the shape of the filter frame. The ribs 232 provide structural support to prevent the filter elements 240 from being drawn through the openings 226 when the filter 104 is exposed to a reduced pressure. A baffle, or diverter 234 may be positioned at the apex 210 of the filter 104 to assist in diverting liquid entering the canister 102 from spraying on the filter elements 240.

The filter 104 of FIG. 2A is illustrated as having two filter elements 240, one for each wall 214 of the frame 202 that includes openings 226. In an alternative embodiment, multiple filter elements 240 may be provided for each wall 214. In one example, one filter element 240 may be provided for each opening 226. The filter elements 240 may be adhesively attached, or attached or bonded by any other means to the walls 214.

The filter elements 240 are preferably liquid-air separators that permit the transmission of gases, but substantially prevent the transmission of liquids through the filter elements 240. In one embodiment, the filter elements 240 are hydrophobic membranes. The filter element 240 may alternatively be any material coated with a hydrophobic material to make the filter element impermeable to liquid. In one illustrative embodiment, the filter element 240 may be a chemically bonded fluorocarbon monomer using a plasma process, thus increasing the hydrophobicity of the filter further. Further, the filter element 240 may be made from or coated with a lipophobic material. Some exemplary filter media materials include foam, spun fiberglass, cotton gauze, polyester, glass fibers, polypropylene, microfibers, porous polymeric membranes, PTFE, and the like.

The frame 202 and the filter elements 240 define an interior region, or filter chamber 244 of the filter 104. As described in more detail below, when the filter 104 is positioned within the canister 102, the interior region 244 of the filter 104 is a space or chamber that is protected from liquid that collects within the canister. By placing the interior region 244 of the filter 104 in fluid communication with the outlet 132 of the canister 102, the reduced pressure source 108 is able to deliver reduced pressure to the interior region 244 without the possibility of the reduced pressure source 108 being contaminated from liquid in the canister 102.

The frame 202 of the filter 104 may be made from any type of material having a sufficient structural rigidity to provide mechanical support for the filter elements 240. Some exemplary materials include plastics, thermoplastics, thermosets, fiber-type materials, metals, metal alloys, and the like. In addition, the frame 202 may be molded, cast, welded or otherwise formed to provide the desired shape. The flange 218 of the frame 202 preferably is made of a material that is capable of being affixed, joined, welded, or otherwise attached to a wall of the canister 102.

Figure 2B:
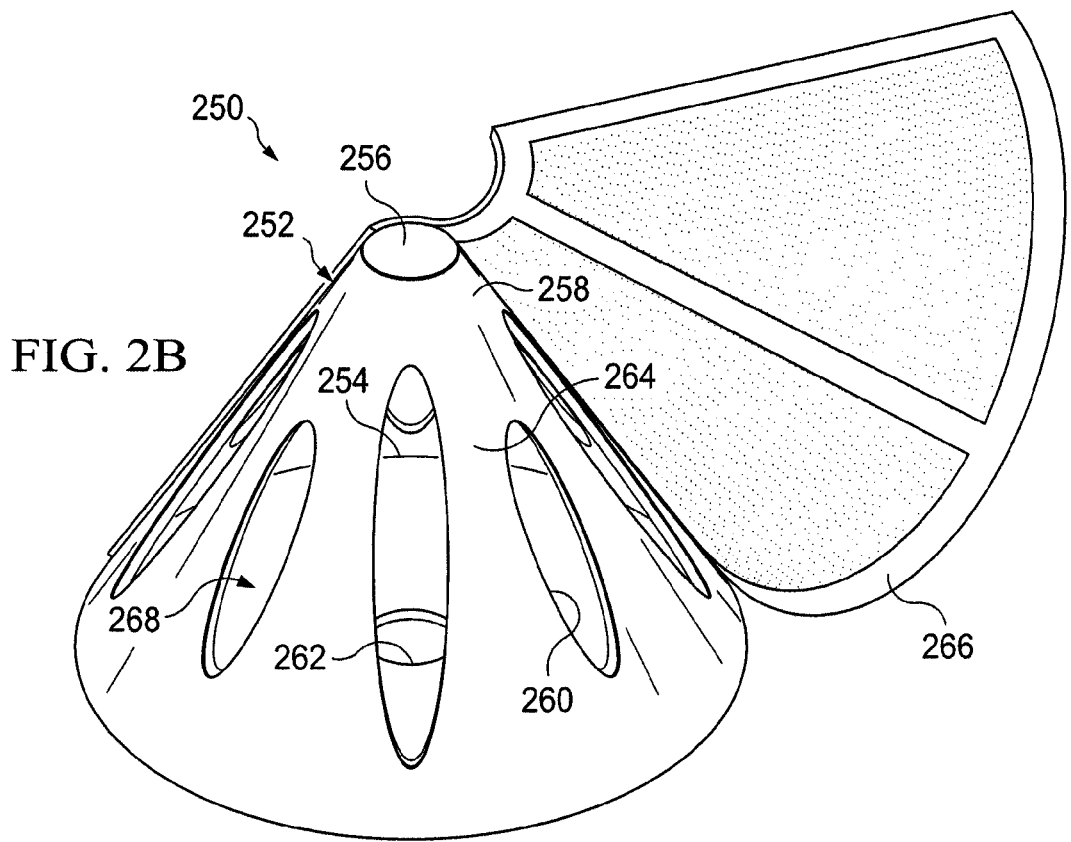
FIG. 2B illustrated an exploded perspective view of a multi-orientation filter according to an illustrative embodiment, the filter being conically shaped.

Referring now to FIG. 2B, in another illustrative embodiment, a filter 250 is provided that is similar in function and operation to, but different in shape than, filter 104. The filter 250 includes a frame 252 that is conically-shaped and includes a base 254 and an apex 256. A conical wall 258 extends from the base 254 to the apex 256 and includes at least one, and preferably a plurality, of openings 260 passing through the conical wall 258. A passage 262 may be positioned in the base 254 to provide fluid communication with the outlet 132 of the canister 102. As previously described with respect to filter 104, the multiple openings 260 of filter 250 form ribs 264 between the openings 260. The openings 260 may be of any shape or size including, without limitation, circular, square, rectangular, ovular, polygonal, irregular, or any other shape.

The filter 250 further includes one or more filter elements 266 to cover the openings 260 in the conical wall 258. In the embodiment illustrated in FIG. 2B, one filter element 266 is illustrated and since the filter element 266 wraps around the conical wall 258, the filter element 266 includes non-planar portions when installed on the frame 252. The ribs 264 provide structural support to prevent the filter element 266 from being drawn through the openings 260 when the filter 250 is exposed to a reduced pressure.

The number of filter elements 266, the means of attaching the filter elements 266 to the frame 252, the function of the filter elements 266, and the material composition of the filter elements 266 is similar to that described for the filter elements 240 of filter 104. The frame 252 and the filter elements 266 define an interior region, or chamber 268 of the filter 250 similar to interior region 244 of filter 104.

Figure 2C:
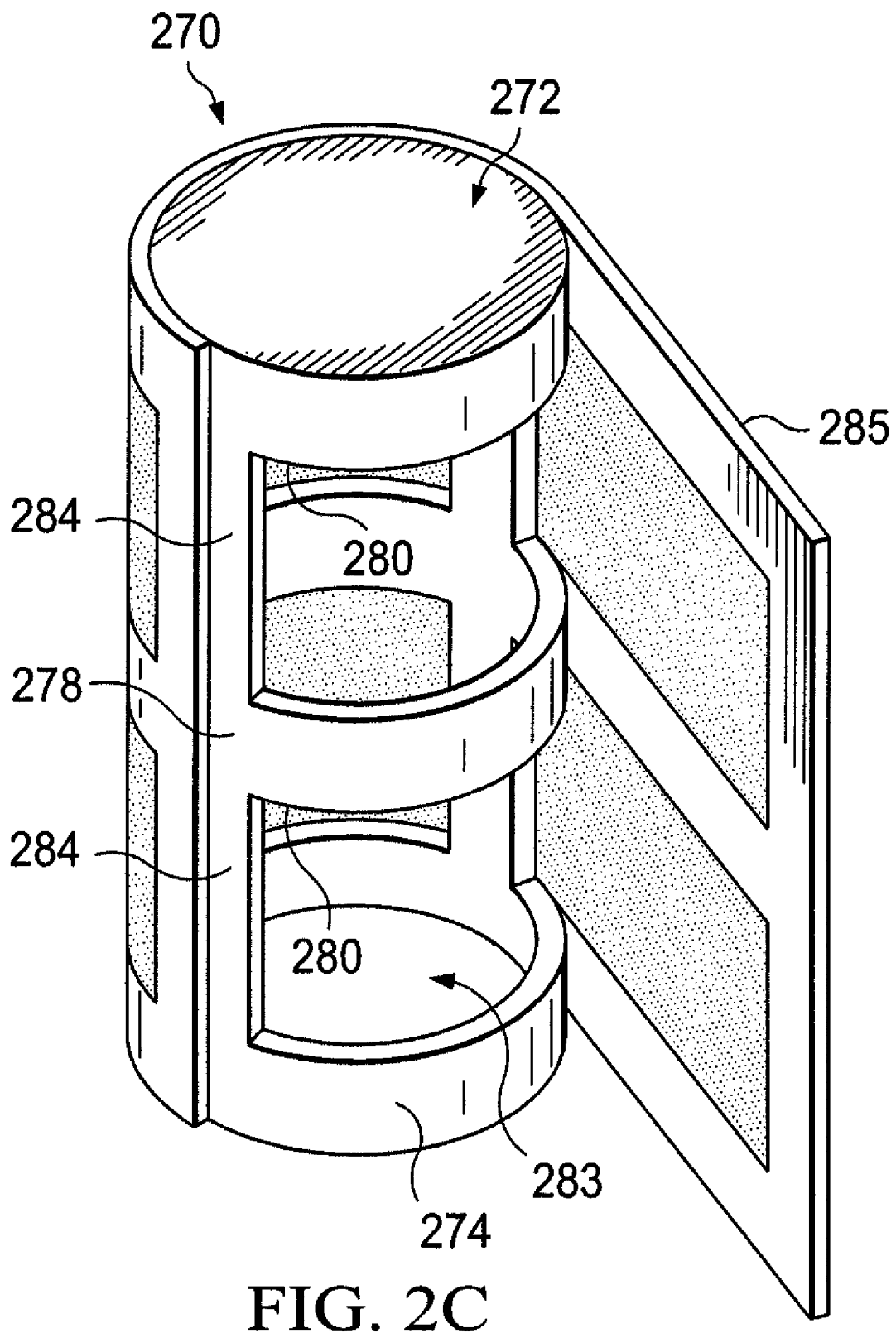
FIG. 2C illustrated an exploded perspective view of a multi-orientation filter according to an illustrative embodiment, the filter being cylindrically shaped.

Referring to FIG. 2C, in another illustrative embodiment, a filter 270 is provided that is similar in function and operation to, but different in shape than, filters 104 and 250. The filter 270 includes a frame 272 that is cylindrically-shaped and includes a cylindrical wall 278 that has at least one and preferably a plurality of openings 280 passing through the cylindrical wall 278. A passage (not shown) may be positioned in a base 274 of the frame 272 to provide fluid communication with the outlet 132 of the canister 102. As previously described with respect to filters 104 and 250, the multiple openings 280 of filter 270 form ribs 284 between the openings 280. The openings 280 may be of any shape or size including, without limitation, circular, square, rectangular, ovular, polygonal, irregular, or any other shape.

The filter 270 further includes one or more filter elements 285 to cover the openings 280 in the cylindrical wall 278. In the embodiment illustrated in FIG. 2C, one filter element 285 is illustrated and since the filter element 285 wraps around the cylindrical wall 278, the filter element 285 includes non-planar portions when installed on the frame 272. The ribs 284 provide structural support to prevent the filter element 285 from being drawn through the openings 280 when the filter 270 is exposed to a reduced pressure.

The number of filter elements 285, the means of attaching the filter elements 285 to the frame 252, the function of the filter elements 285, and the material composition of the filter elements 285 is similar to that described for the filter elements 240 of filter 104. The frame 272 and the filter elements 285 define an interior region, or chamber 283 of the filter 270 similar to interior region 244 of filter 104.

Figure 2D:
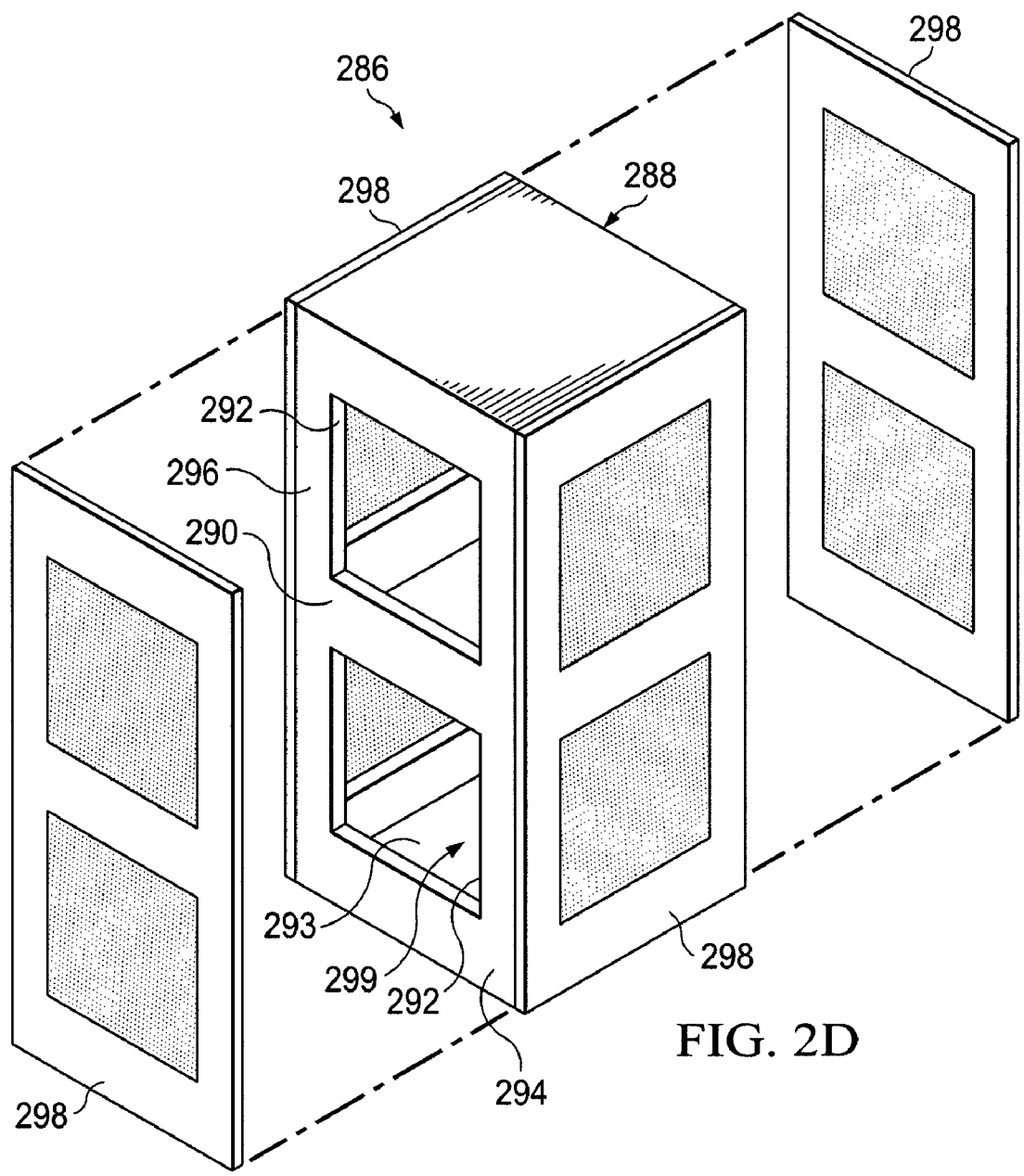
FIG. 2D illustrated an exploded perspective view of a multi-orientation filter according to an illustrative embodiment, the filter being rectangular cubically shaped.

Referring to FIG. 2D, in another illustrative embodiment, a filter 286 is provided that is similar in function and operation to, but different in shape than, filters 104, 250, 270. The filter 286 includes a frame 288 that is cubically or rectangular cubically-shaped and includes a rectangular-cubical wall 290 that has at least one and preferably a plurality of openings 292 passing through the wall 290. A passage 293 may be positioned in a base 294 of the frame 288 to provide fluid communication with the outlet 132 of the canister 102. As previously described with respect to filters 104, 250, and 270, the multiple openings 292 of filter 286 form ribs 296 between the openings 292. The openings 292 may be of any shape or size including, without limitation, circular, square, rectangular, ovular, polygonal, irregular, or any other shape.

The filter 286 further includes one or more filter elements 298 to cover the openings 292 in the wall 290. In the embodiment illustrated in FIG. 2D, one filter element 298 is illustrated on each of the walls 290, and each filter element 298 is substantially planar when installed on the frame 288. The ribs 296 provide structural support to prevent the filter element 298 from being drawn through the openings 292 when the filter 286 is exposed to a reduced pressure.

The number of filter elements 298, the means of attaching the filter elements 298 to the frame 252, the function of the filter elements 298, and the material composition of the filter elements 298 is similar to that described for the filter elements 240 of filter 104. The frame 288 and the filter elements 298 define an interior region, or chamber 299 of the filter 286 similar to interior region 244 of filter 104.

Referring still to FIG. 1, but also to FIGS. 3-6, the canister 102 and the positioning of the filter 104 within the canister 102 are described in more detail. While the filters described herein may be used with canisters of any particular shape and size, canister 102 is substantially cubical or rectangular cubical in shape. Canister 102 includes six walls: a first wall 302 in which the outlet 132 of the canister 102 is disposed, a second wall 304 in which the inlet 116 of the canister 102 is disposed, a third wall 306 which represents the bottom wall of the canister 102 in FIG. 1, a fourth wall 308 which represents the top wall of the canister 102 in FIG. 1, a fifth wall 310, and a sixth wall 312. Together, the six walls define an interior chamber, or interior space 318 of the canister 102.

The filter 104 is positioned within the interior space 318 of the canister 102 such that the base 206 of the filter 104 is adjacent the first wall 302. The passage 222 in the base 206 of the filter 104 is aligned with the outlet 132 of the canister 102 such that reduced pressure from the reduced pressure source 108 may be communicated to the interior region 244 of the filter 104. The base 206 of the filter 104 is preferably connected to and supported by the first wall 302 in any number of ways including, without limitation, welding, gluing or other fastening means. Preferably, a sealing connection is provided between the outlet 132 and/or conduit 128 and the interior region 244. This sealing connection prevents direct fluid communication between the interior space 318 of the canister 102 and the conduit 128. Instead, any fluid communication between the interior space 318 of the canister 102 and the conduit 128 must occur via the interior region 244 of the filter 104. Due to the presence of the liquid-blocking filter elements 240, only gases from the interior space 318 of the canister 102 may pass through the interior region 244 to the conduit 128.

Although the positioning of the inlet 116 and outlet 132 of the canister 102 may vary, in the embodiment illustrated in FIG. 1, the inlet 116 and outlet 132 are disposed in opposing walls of the canister 102. The inlet 116 of the canister 102 is generally centered in the second wall 304, and the outlet 132 is generally centered in the first wall 302. The placement of the filter 104 is such that the base 206 completely covers the first wall 302, and the apex 210 of the filter 104 is centrally positioned adjacent the inlet 116. Similarly, filters of other shapes may be similarly positioned within a canister similar to canister 102. For example, a conically-shaped filter such as filter 250 could be positioned in the canister 102 such that the apex 256 of filter 250 is centrally aligned with the inlet 116. Filter 270 and filter 286, or filters of other shapes, may similarly be positioned in the canister 102 as an alternative to filter 104.

Figure 3:
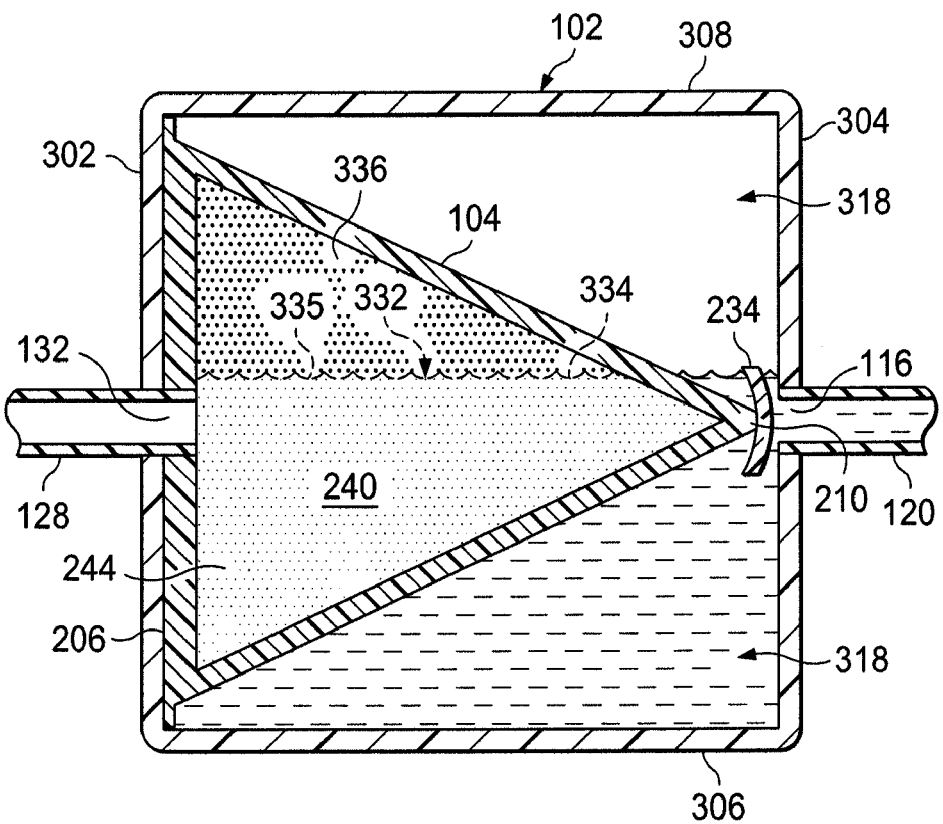
FIG. 3 illustrates a cross-sectional view of the liquid-collection canister of FIG. 1 taken at 3-3.

The interior space 318 of the canister forms a first space where liquid from the tissue site 101 is collected. The interior region 244 of the filter 104 forms a second space, which is a dry space that is substantially protected from liquid. The interior region 244 allows the passage of reduced pressure between the reduced pressure source 108 and the interior space 318 of the canister 102. When a reduced pressure is applied by the reduced pressure source 108 to the canister 102, the reduced pressure is delivered to the tissue site 101, which results in liquid 332 at the tissue site 101 being drawn into the interior space 318 of the canister 102. Referring more specifically to FIG. 3, which represents an orientation of the canister with the third wall 306 down (similar to that illustrated in FIG. 1), the liquid 332 begins to fill the interior space 318 of the canister 102 but is substantially prevented from passing through the filter elements 240 to enter the interior region 244 of the filter 104. The liquid 332 includes a surface 334 that is substantially planar and forms a liquid plane 335. As the liquid 332 rises within the canister 102, any portion of the filter elements 240 below the surface 334 of the liquid 332 will no longer allow transmission or flow of gas between the interior space 318 and the interior region 244. In other words, the reduced pressure will no longer be delivered or transferred to the interior space 318 through the portion of the filter element 240 that is covered in liquid 332. A dry region 336 of the filter element 240 located above the liquid surface 334 (the dry region 336 is shaded darker in FIG. 3) continues to allow flow of gas or transmission of reduced pressure between the interior space 318 and the interior region 244. As long as a portion of the filter element 240 remains uncovered by liquid 332, the filter element will continue to permit gas flow and transmission of reduced pressure.

Figure 4:
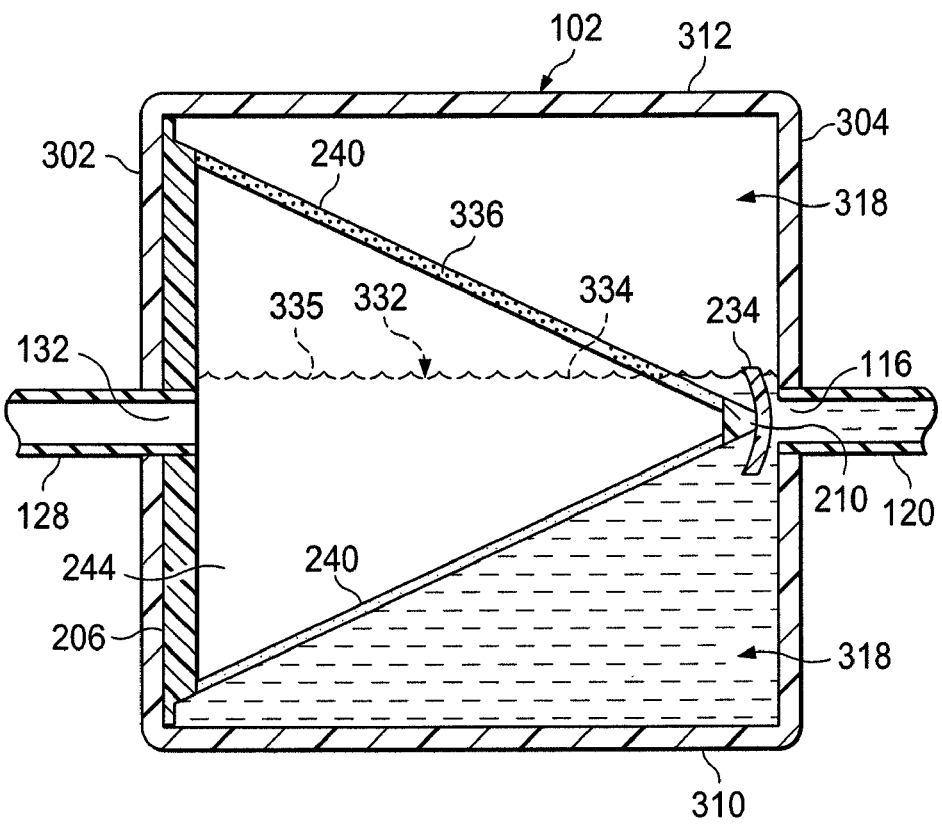
FIG. 4 illustrates a cross-sectional view of the liquid-collection canister of FIG. 1 similar to the cross-section of FIG. 3 but with a side wall of the canister oriented downward.
Figure 5:
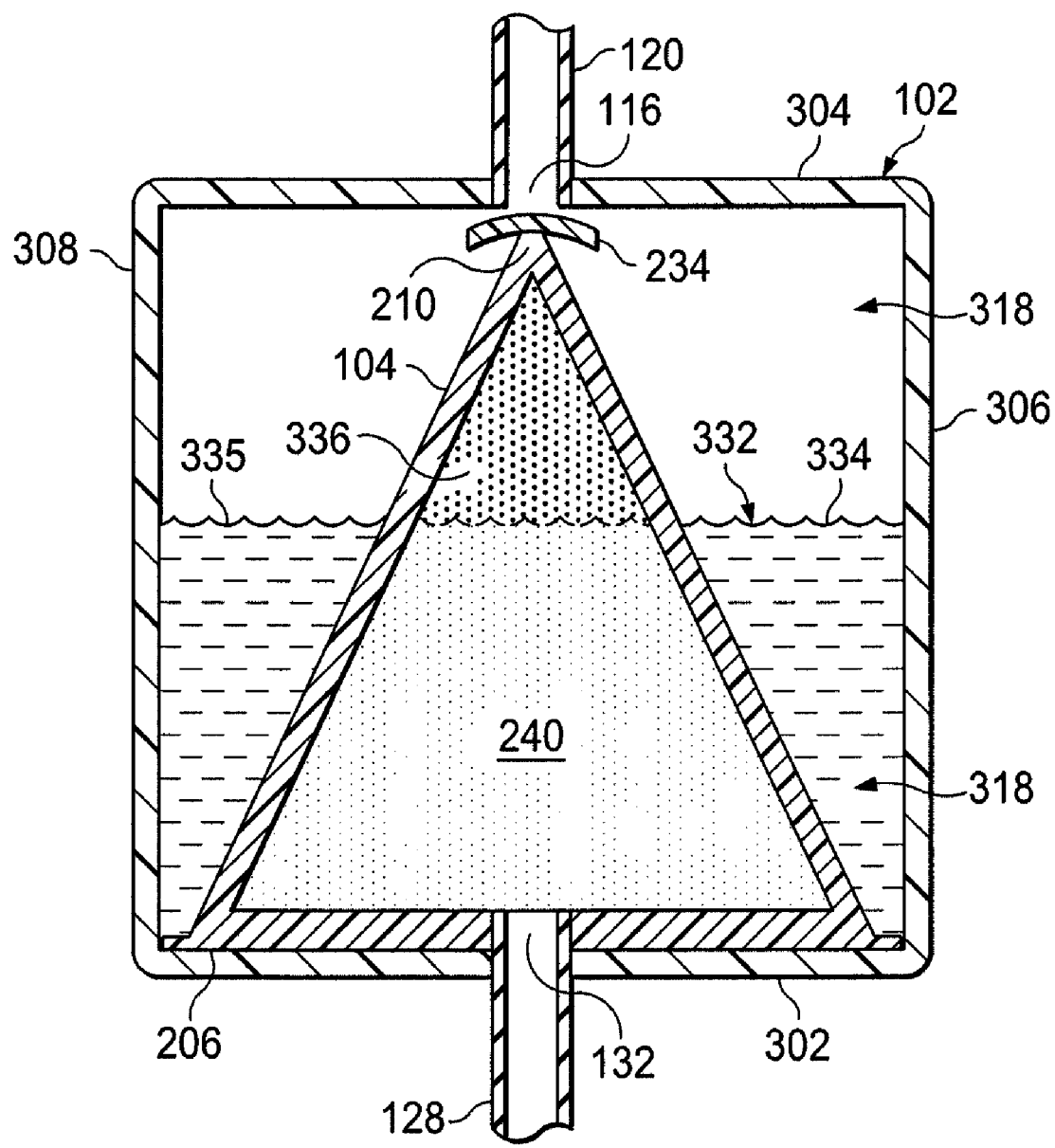
FIG. 5 illustrates a cross-sectional view of the liquid-collection canister of FIG. 1 similar to the cross-section of FIG. 3 but with an outlet wall of the canister oriented downward.
Figure 6:
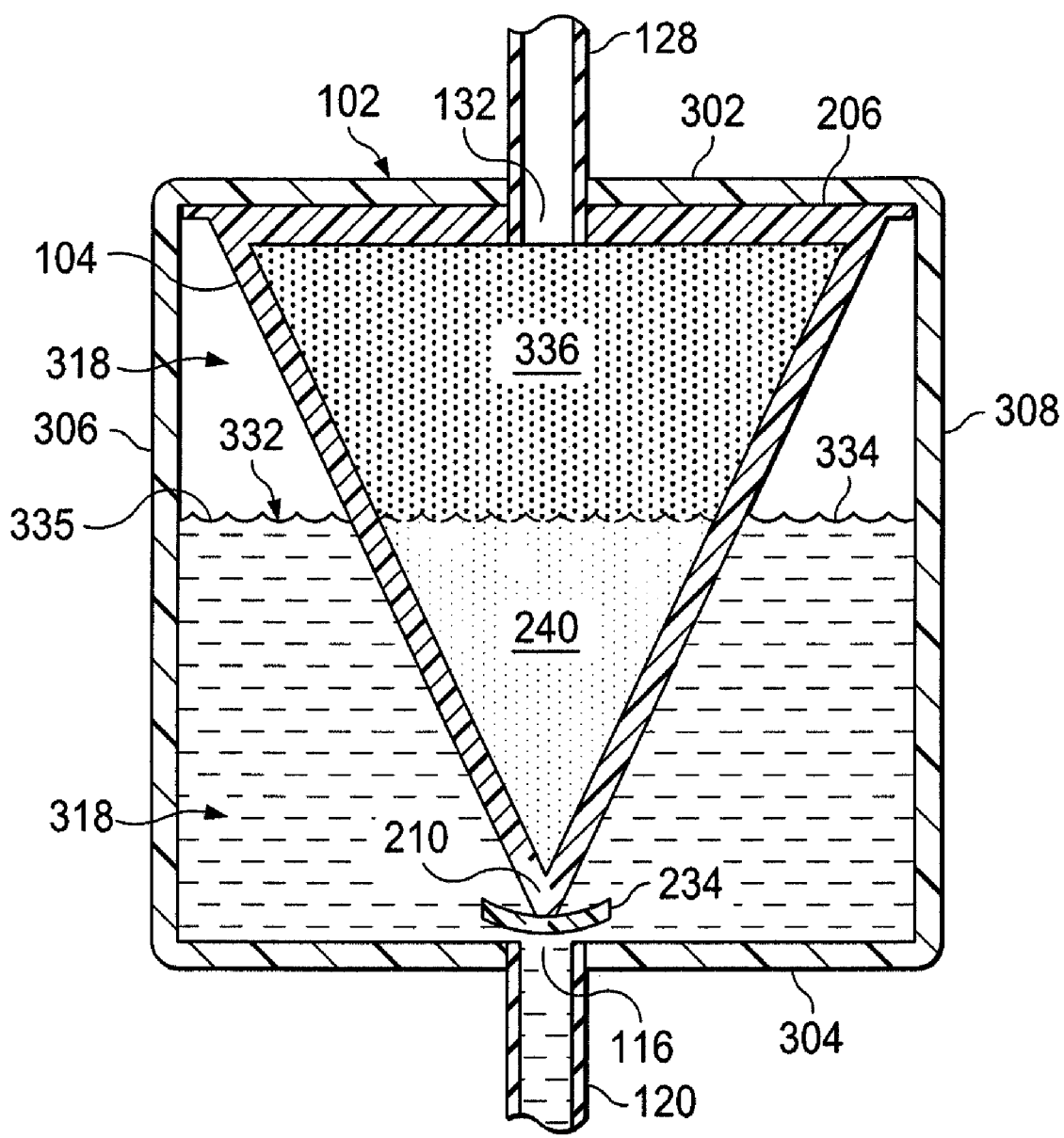
FIG. 6 illustrates a cross-sectional view of the liquid-collection canister of FIG. 1 similar to the cross-section of FIG. 3 but with an inlet wall of the canister oriented downward.

In FIG. 4, the filter 104 is illustrated in an orientation in which fifth wall 310 is positioned in a downward position. In FIG. 5, the filter 104 is illustrated in an orientation in which first wall 302 is positioned in a downward position. In FIG. 6, the filter 104 is illustrated in an orientation in which second wall 304 is positioned in a downward position. In each of the canister orientations illustrated in FIGS. 4-6, the presence of liquid within the interior space 318 of the canister 102 blocks transmission of gas through the portions of the filter elements 240 beneath the surface 334 of the liquid. However, gas flow and thus reduced pressure transmission between the reduced pressure source 108 and the tissue site 101 continues due to the presence of the dry region 336 of the filter elements 240 above the surface 334 of the liquid 332.

It is important to note that in each of the orientations of the canister 102 shown in FIGS. 3-6, as well as in additional orientations of the canister 102 that have not been illustrated, the shape, size, and positioning of the filter 104 within the canister 102 allow the canister to continue to transmit reduced pressure even as the level of liquid 332 within the canister rises to and beyond the volume of the interior space 318 being half full of liquid. This particular feature of the filter 104, and of the other filters described herein, is not possible with existing filters that often include a single, planar filter element, or multiple filter elements that are arranged in a co-planar arrangement. With these types of filters, a particular orientation of the filter (usually the orientation that results in the planar filter element being positioned at the bottom of the canister) will allow only a small amount of liquid collection. As the liquid covers the filter element completely, transmission of reduced pressure through the canister ceases.

The success of the filter 104 at allowing large-volume liquid collection in any orientation of the canister 102 is due in part to the large and multi-faceted filter elements 240 that are a part of the filter 104. The tapered nature of the filter 104 increases the liquid-collecting volume of the interior space 318, but also provides a large surface area for the filter elements 240. The filter elements 240 of filter 104 are substantially planar, but the plane associated with each filter element 240 is obliquely angled relative to the planes of other filter elements 240. This angled relationship between the filter elements 240 results in at least a portion of one of the filter elements 240 being not parallel to the liquid plane 335 of the liquid 332 in any particular orientation of the canister 102. Since there is almost always a filter element 240 that will not be parallel to the surface 334 of the liquid 332, the ability of the filter elements 240 to continue gas transmission during higher volumes of liquid collection is improved.

The baffle 234 may be positioned on the filter 104 or canister 102 to further prevent the liquid 332 from contacting the filter elements 240 as the fluid enters the inlet 116 of the canister 102 and flows downward with gravity to the bottom of the canister 102. Since even incidental contact with liquid or bubbles formed by liquid entering the canister may result in protein deposition on the filter elements 240, and thus premature blockage of gas transmission by the filter elements 240, the baffle 234 may serve a valuable role in preventing premature contact between the liquid 332 and the filter elements 240.

While it may be generally desirable to position the filter 104 such that the base 206 is against the wall of the canister 102 having the outlet 132 (i.e. in FIG. 1, first wall 302), the base 206 instead may be positioned against a wall of the canister 102 that does not include the outlet. For example, the filter 104 may be positioned with base 206 adjacent the third wall 306, the fourth wall 308, the fifth wall 310, or the sixth wall 312. In such an arrangement, the outlet 132 may be fluidly connected to the interior region 244 of the filter 104 by a conduit that is plumbed through the base 206, the apex 210, or one of the walls 214 of the filter 104. It should also be noted that while the outlet 132 and inlet 116 of the canister 102 have been described as being located in opposing walls of the canister 102, the outlet 132 and inlet 116 may be positioned in adjacent walls, or even in the same wall depending on the size, shape, and positioning of the filter 104.

Figure 7:
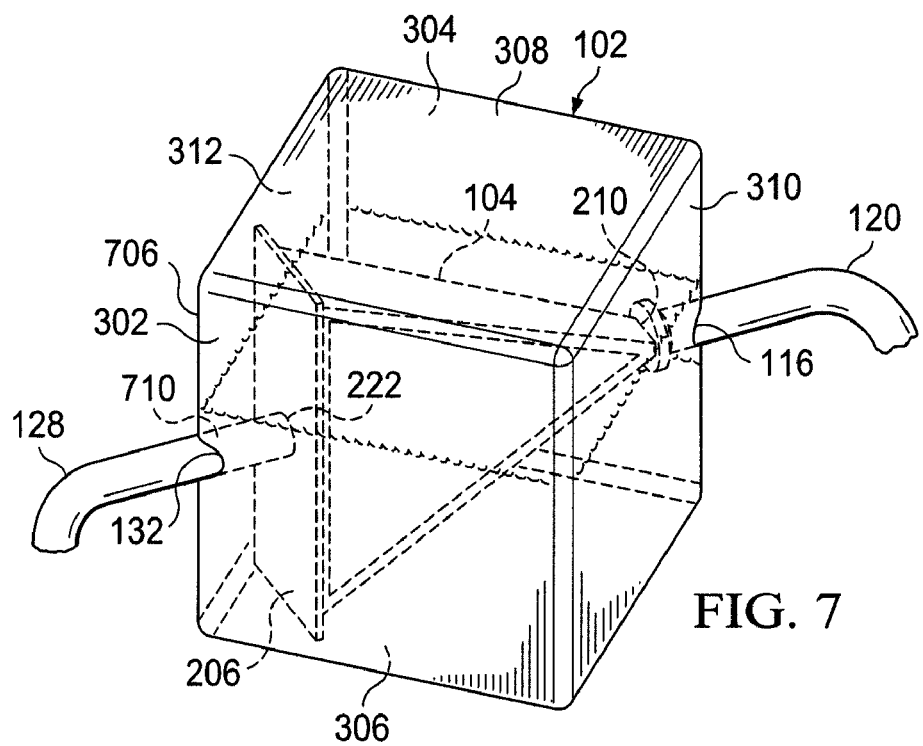
FIG. 7 illustrates a perspective view of the multi-orientation filter of FIG. 1 positioned in liquid-collection canister according to an illustrative embodiment.

In another example, such as that illustrated in FIG. 7, the filter 104 may be positioned such that base 206 does not lie flat against a wall of the canister. Instead, the filter 104 is positioned such that the base 206 is adjacent a corner 706 formed between two walls of the canister 102. The outlet 132 is positioned within the corner 706, and a conduit 710 provides communication between the outlet 132 and the passage 222 of the base 206. Similarly, filters of other shapes such as those described herein may also be positioned as illustrated in FIG. 7.

Figure 8:
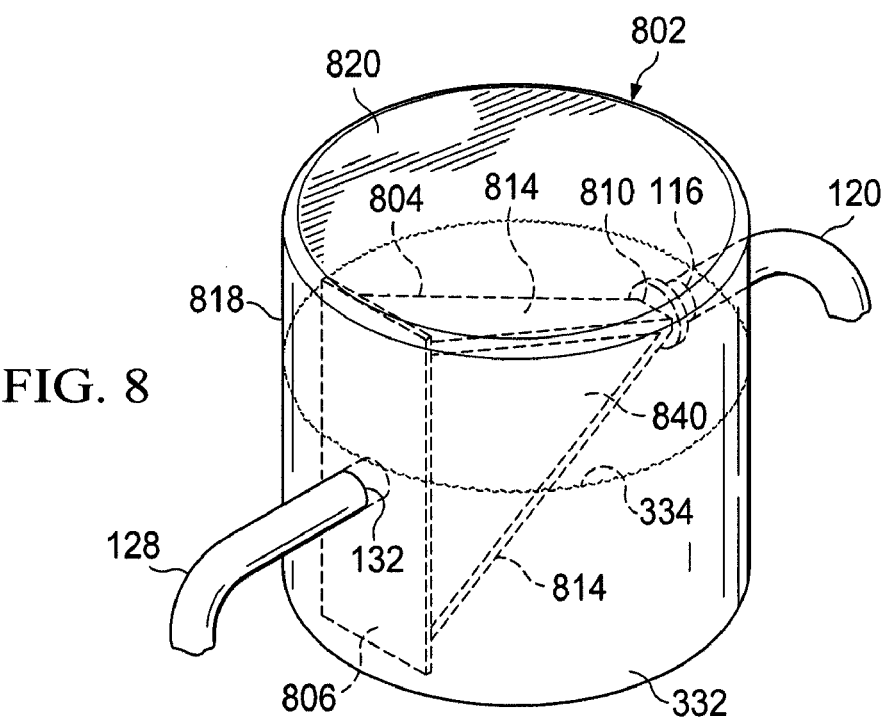
FIG. 8 illustrates a perspective view of the multi-orientation filter of FIG. 1 positioned in a liquid-collection canister according to an illustrative embodiment.

Referring to FIG. 8, a filter 804 similar in shape to filter 104 may be positioned in a cylindrically-shaped canister 802. In the configuration illustrated in FIG. 8, the filter 804 includes a base 806, an apex 810, a plurality of walls 814, and a plurality of filter elements 840. The base 806 is positioned adjacent a cylindrical wall 818 of the canister 802, although in another embodiment, the base 806 could be positioned against one of two end walls 820 of the canister 802. The canister 802 and filter 804 are similar in function to the canister 102 and filter 104, and the filter 804 is similarly capable of allowing continued transmission of reduced pressure and collection of liquid in multiple orientations of the canister 802.

Figure 9:
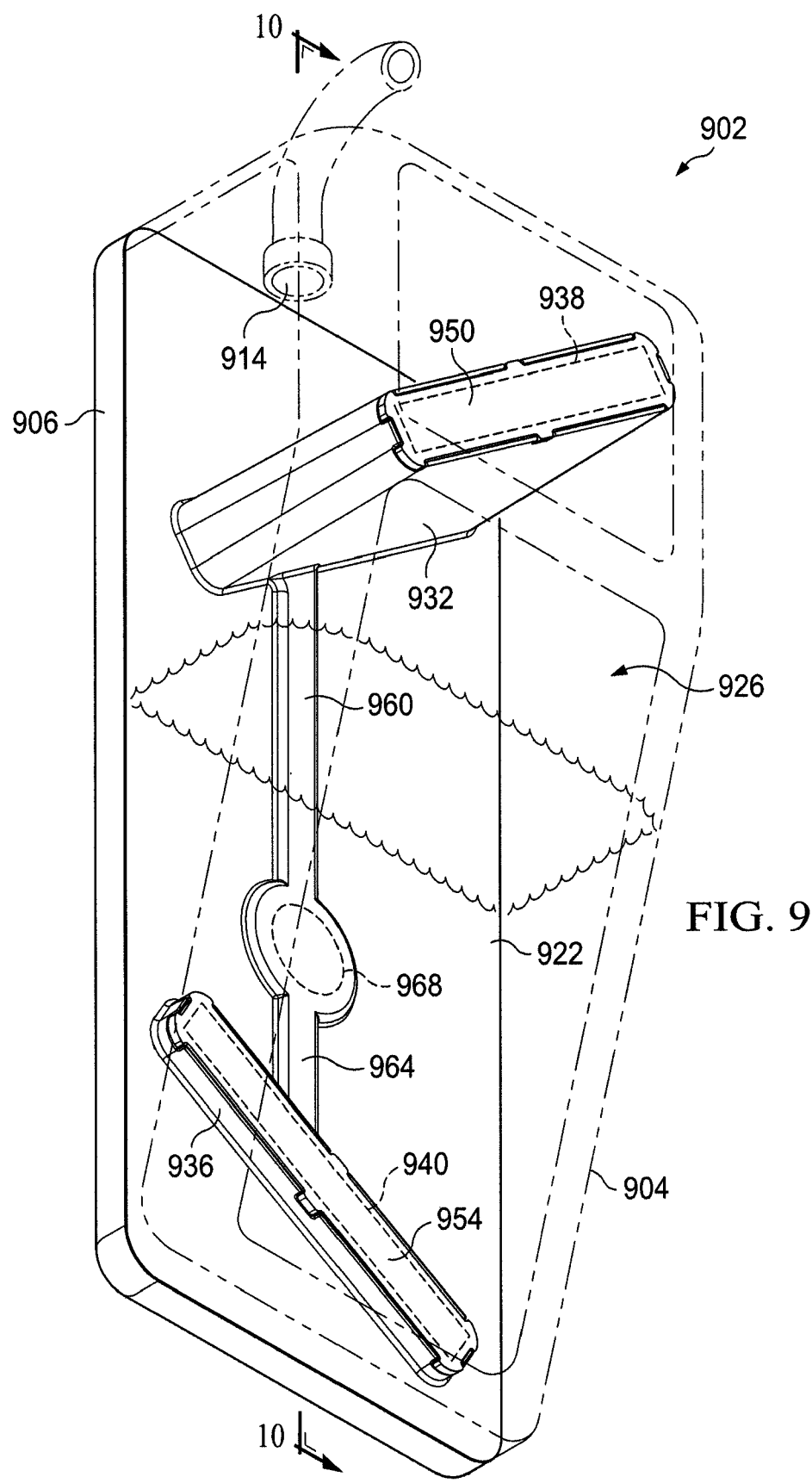
FIG. 9 illustrates a perspective view of a liquid collection canister according to an illustrative embodiment, the canister having a multi-orientation filter.
Figure 10:
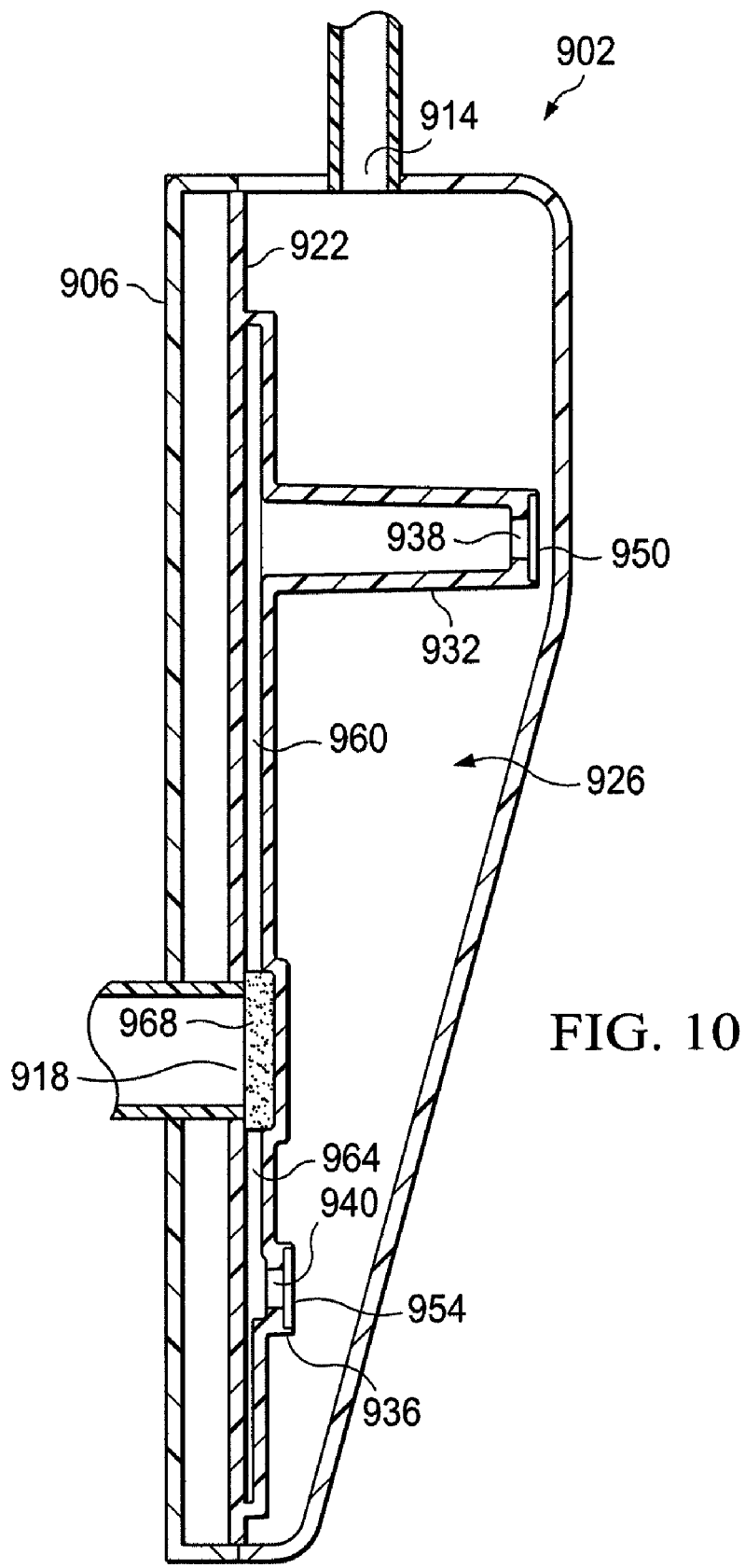
FIG. 10 illustrates a cross-sectional view of the liquid-collection canister of FIG. 9 taken at 10-10.

Referring to FIGS. 9 and 10, a canister 902 according to an illustrative embodiment may be used with a reduced pressure treatment system similar to reduced pressure treatment system 100. Canister 902 includes a basin 904 and a lid 906 that are capable of complementary engagement to form a substantially sealed interior chamber, or interior space 910 within the canister. The canister 902 includes an inlet 914 that may be fluidly connected to a reduced pressure dressing and an outlet 918 that may be fluidly connected to a reduced pressure source.

The lid 906 forms a substantially planar wall 922 of the canister 902. A filter 926 is positioned on the wall 922 and includes a first chamber 932 and a second chamber 936, both of which extend from the wall 922. The first chamber 932 includes an opening 938 disposed at an end of the first chamber 932 opposite the wall 922, and the second chamber 936 includes an opening 940 disposed at an end of the second chamber 936 opposite the wall 922. The opening 938 of the first chamber 932 allows fluid communication between the interior space 910 and the first chamber 932, while the opening 940 of the second chamber 936 allows fluid communication between the interior space 910 and the second chamber 936. The volume of the first chamber 932 is greater than the volume of the second chamber 936 due in large part to the variation in distance that each chamber extends from the wall 922. The distance between the opening 938 of the first chamber 932 and the wall 922 is greater than the distance between the opening 940 of the second chamber 936 and the wall 922.

Each of the openings 938, 940 are covered with a filter element similar in function and material composition to the filter elements described herein. A first filter element 950 is positioned over the opening of the first chamber 932, and a second filter element 954 is positioned over the opening of the second chamber 936. Both the first and second filter elements 950, 954 may be substantially planar, and the variation in distance between each filter element and the wall relative to one another places the filter elements 950, 954 in separate planes. In the embodiment illustrated in FIGS. 9 and 10, the plane associated with filter element 950 is substantially parallel to the plane associated with filter element 954, and both planes are substantially parallel to the wall 922. In another embodiment, the filter elements may be oriented such that the planes associated with the filter elements are not parallel.

In the embodiment illustrated in FIGS. 9 and 10, both the first chamber 932 and the second chamber 936 are fluidly connected to the outlet 918 of the canister 902. A first channel 960 is positioned along the wall 922 and is fluidly connected between the first chamber 932 and the outlet 918. A second channel 964 is positioned along the wall 922 and is fluidly connected between the second chamber 936 and the outlet 918. An odor filter 968, such as for example a charcoal filter, may be positioned at a junction of the first channel 960 and the second channel 964 to reduce odor associated with gases withdrawn from the canister 902.

The interior space 910 of the canister 902 forms a first space where liquid from a tissue site may be collected. The first chamber 932 and the second chamber 936 form a second space, which is a dry space that is substantially protected from liquid. The first and second chambers 932, 936 allow the passage of reduced pressure between a reduced pressure source and the interior space 910 of the canister 902. When a reduced pressure is applied by the reduced pressure source to the canister 902, the reduced pressure is delivered to the tissue site, which results in liquid at the tissue site being drawn into the interior space 910 of the canister 902. Similar in operation to the canister 102 illustrated in FIGS. 3-6, the liquid begins to fill the interior space 910 of the canister 902 but is substantially prevented from passing through the filter elements 950, 954 to enter the first and second chambers 932, 936 of the filter 926. The sizing, positioning, and arrangement of the first and second filter elements 950, 954 is such that substantial amounts of liquid collection are permitted in any particular orientation of the canister 902. Similar to filter 104, filter 926 allows the canister to continue to transmit reduced pressure even as the level of liquid within the canister rises to and beyond the volume of the interior space 910 being half full of liquid. This particular feature of the filter 926 is possible due to the multi-planar positioning of the filter elements 950, 954 relative to one another, and due to the spaced positioning of the filter elements 950, 954.

The canisters 102, 802 and 902 may be any type of material of sufficient rigidity and structural integrity to withstand the reduced pressure required for reduced pressure treatment and to contain liquid therein. Some exemplary materials of the canisters are plastics, polymers, thermoplastics, metals, metal alloys, composition material, fiber-type materials, and the like. The canisters may have a plurality of individual sides that are affixed, joined, and/or welded together to create the desired shape, e.g., rectangular or cylindrical, or may be a molded single or multi-part housing. The plastics described herein may be a substance or structure capable of being shaped or molded with or without the application of heat, a high polymer, usually synthetic, combined with other ingredients such as curatives, fillers, reinforcing agents, plasticizers, etc. Plastics can be formed or molded under heat and pressure in its raw state and machined to high dimensional accuracy, trimmed and finished in its hardened state. The thermoplastic type can be resoftened to its original condition by heat. In addition, the plastics may mean engineered plastics such as those that are capable of sustaining high levels of stress and are machinable and dimensionally stable. Some exemplary plastics are nylon, acetyls, polycarbonates, ABS resins, PPO/styrene, and polybutylene terephthalate. The thermoplastics described herein may be high polymers that softens when exposed to heat and return to their original condition when cooled to room temperature. Generally, it may apply to synthetics such as polyvinylchloride, nylons, fluorocarbons, linear polyethylene, polyurethane prepolymer, polystyrene, polypropylene, and cellulosic and acrylic resins, for example.

Each of the filters described herein may be varied in size or shape to better accommodate a canister of a particular size or shape. While several canister shapes have been illustrated and described, use of the filters described herein, and the advantages that these filters provide, is not limited to any particular shape of canister.

While some of the filters presented herein have been described as having a single interior space or chamber, the number of filter chambers is not limited. Multiple filter chambers that are either independently or jointly connected to the canister outlet or multiple canister outlets may be employed, again depending at least partially upon the size and shape of the canister. Similarly, multiple filter elements may be used to increase the time that the filter maintains gas transmission during liquid collection activities.

The filters and liquid-collection canisters described herein may be used as part of a process or method for collecting liquid from a tissue site. In one embodiment, a method of collecting liquid from a tissue site may include applying a reduced pressure to a second space of a canister such as the liquid-collection canisters described with reference to FIGS. 1-10. The second space of the liquid-collection canister has an opening to allow communication with a first space of the canister. The opening is covered by a non-planar filter element that allows gaseous communication through the non-planar filter element such that the reduced pressure is communicated to the first space of the canister. Liquid is drawn into the first space, and flow through the non-planar filter element is filtered to substantially prevent the liquid from entering the second space.

In another illustrative embodiment, a method of collecting liquid from a tissue site includes applying a reduced pressure to a second space of a canister. The second space has a plurality of openings to allow communication with a first space of the canister. The openings are covered by a plurality of liquid-air separators, and at least two of the plurality of liquid-air separators are substantially planar and located within different planes. Gaseous communication is allowed through the liquid-air separators such that the reduced pressure is communicated to the first space of the canister. The liquid is drawn into the first space, and flow through the liquid-air separators is filtered to substantially prevent the liquid from entering the second space.

In still another illustrative embodiment, a method of collecting liquid from a tissue site includes applying a reduced pressure to a first chamber and a second chamber of a canister. The first and second chambers each extend from a wall of the canister and each include an opening at an end of the chamber opposite the wall. The opening of the first chamber is covered by a first filter element, and the opening of the second chamber is covered by a second filter element. A distance from the opening of the first chamber to the wall is greater than a distance from the opening of the second chamber to the wall. The method further includes allowing gaseous communication through the first and second filter elements such that the reduced pressure is communicated to a first space of the canister. The liquid is drawn into the first space, and flow through the first and second filter elements is filtered to substantially prevent the liquid from entering the first and second chambers.

The filters and liquid-collection canisters described herein may also be used as part of a process or method for administering reduced pressure treatment to a tissue site. In one embodiment, the method includes applying a reduced pressure to a second space of a canister such as the canisters described herein. The second space has an opening to allow communication with a first space of the canister, and the opening is covered by a non-planar filter element. Gaseous communication is allowed through the non-planar filter element such that the reduced pressure is communicated to the first space of the canister. The reduced pressure is communicated to the tissue site. A liquid is drawn from the tissue site into the first space, and flow through the non-planar filter element is filtered to substantially prevent the liquid from entering the second space.

In another illustrative embodiment, a method of administering reduced pressure treatment to a tissue site may include applying a reduced pressure to a second space of a canister similar to the canisters described herein. The second space has a plurality of openings to allow communication with a first space of the canister. The openings are covered by a plurality of liquid-air separators, and at least two of the plurality of liquid-air separators are substantially planar and located within different planes. The method further includes allowing gaseous communication through the liquid-air separators such that the reduced pressure is communicated to the first space of the canister. The reduced pressure is communicated to the tissue site. A liquid is drawn from the tissue site into the first space, and flow through the liquid-air separators is filtered to substantially prevent the liquid from entering the second space.

In yet another illustrative embodiment, a method of administering reduced pressure treatment to a tissue site includes applying a reduced pressure to a first chamber and a second chamber of a canister such as the canisters described herein. The first and second chambers each extend from a wall of the canister, and each include an opening at an end of the chamber opposite the wall. The opening of the first chamber is covered by a first filter element, and the opening of the second chamber is covered by a second filter element. A distance from the opening of the first chamber to the wall is greater than a distance from the opening of the second chamber to the wall. Gaseous communication is allowed through the first and second filter elements such that the reduced pressure is communicated to a first space of the canister. The reduced pressure is communicated to the tissue site. A liquid is drawn from the tissue site into the first space, and flow through the first and second filter elements is filtered to substantially prevent the liquid from entering the first and second chambers.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure treatment system for applying reduced pressure treatment to a tissue site, the system comprising:
   a liquid-collection canister comprising:
      a first space configured to collect the liquid from the tissue site;
      a second space configured to receive a reduced pressure;
      a plurality of liquid-air separators positioned within the canister between the first space and the second space such that the liquid in the first space is substantially prevented from entering the second space, the plurality of liquid-air separators allowing transfer of a gas between the second space and the first space, at least two of the plurality of liquid-air separators being substantially planar and each of the two located within different planes, wherein a first plane associated with a first of the two liquid-air separators is parallel to a second plane associated with a second of the two liquid-air separators;
      a canister inlet associated with the first space; and
      a canister outlet associated with the second space;
   a reduced pressure source in fluid communication with the canister outlet to deliver a reduced pressure to the second space; and
   a manifold positioned at the tissue site and in fluid communication with the canister inlet to distribute the reduced pressure to the tissue site.

2. The system of claim 1, wherein the liquid-air separator is a hydrophobic filter element.

3. The system of claim 1, wherein:
   the plurality of liquid-air separators are positioned on a frame of a filter positioned within the liquid-collection canister; and
   the frame of the filter is pyramid-shaped with a base, an apex, and four walls extending between the base and the apex, the frame having an opening in at least two of the walls allowing communication between the first space and the second space, at least one of the plurality of liquid-air separators covering each opening.

4. The system of claim 3, wherein each of the four walls includes openings.

5. The system of claim 3, wherein:
   the canister includes at least one substantially planar wall; and
   the base of the frame is positioned on the substantially planar wall and the apex extends toward an opposite wall of the canister.

6. The system of claim 3, wherein:
the canister includes at least two substantially planar walls that intersect to form a corner; and
the base of the frame is positioned adjacent the corner within the canister and the apex extends toward an opposite corner of the canister.

7. The system of claim 1, wherein:
the plurality of liquid-air separators are positioned on a frame of a filter positioned within the liquid-collection canister; and
the frame of the filter is rectangular cube-shaped with a base, an upper wall, and four side walls extending between the base and the upper wall, the frame having an opening in at least two of the side walls allowing communication between the first space and the second space, at least one of the plurality of liquid-air separators covering each opening.

8. The system of claim 7, wherein each of the four side walls includes openings.

9. The system of claim 7, wherein:
the canister includes at least one substantially planar wall; and
the base of the frame is positioned on the substantially planar wall and the side walls extend toward an opposite wall of the canister.

10. The system of claim 7, wherein:
the canister includes at least two substantially planar walls that intersect to form a corner; and
the base of the frame is positioned adjacent the corner within the canister and the side walls extend toward an opposite corner of the canister.

11. The system of claim 1, wherein the plurality of liquid-air separators is positioned within the liquid-collection canister such that, in any particular orientation of the canister, a portion of at least one of the liquid-air separators is not parallel to a liquid plane associated with the liquid in the first space.

12. The system of claim 1, wherein the plurality of liquid-air separators is positioned within the canister such that, for any particular orientation of the canister, at least one of the liquid-air separators permits gaseous communication between the first space and the second space when half or more of the volume of the first space is occupied by the liquid.

13. A reduced pressure treatment system for applying reduced pressure treatment to a tissue site, the system comprising:
a liquid-collection canister comprising:
a first space configured to collect the liquid from the tissue site; and
a filter disposed on a wall of the canister, the filter having a first chamber extending from the wall of the canister and including an opening at an end of the first chamber opposite the wall, the filter having a second chamber extending from the wall of the canister and including an opening at an end of the second chamber opposite the wall, the opening of the first chamber allowing communication between the first space and the first chamber, the opening of the second chamber allowing communication between the first space and the second chamber, a distance from the opening of the first chamber to the wall being greater than a distance from the opening of the second chamber to the wall;
a first filter element positioned over the opening of the first chamber;
a second filter element positioned over the opening of the second chamber;
a canister inlet to allow communication with the first space; and
a canister outlet to allow communication with the first and second chambers;
a reduced pressure source in fluid communication with the canister outlet to deliver a reduced pressure to the first and second chambers; and
a manifold positioned at the tissue site and in fluid communication with the canister inlet to distribute the reduced pressure to the tissue site.

14. The system of claim 13, wherein the first and second filter elements are each substantially planar and are substantially parallel to the wall.

15. The system of claim 13, wherein the first chamber and the second chamber are fluidly connected to an outlet of the canister.

16. The system of claim 13, wherein;
the first chamber is fluidly connected to a first outlet of the canister; and
the second chamber is fluidly connected to a second outlet of the canister.

17. The system of claim 13, wherein the first and second chambers are rectangular cube-shaped.

18. The system of claim 13, wherein the first and second filter elements are positioned within the liquid-collection canister such that, in any particular orientation of the canister, a portion of at least one of the first and second filter elements is not parallel to a liquid plane associated with a surface of the liquid in the first space.

19. The system of claim 13, wherein the first and second filter elements are positioned within the liquid-collection canister such that, for any particular orientation of the canister, the at least one of the first and second filter elements continues to permit gaseous communication between the first space and at least one of the first and second chambers when half or more of the volume of the first space is occupied by the liquid.

* * * * *